(12) United States Patent
Yeom

(10) Patent No.: US 8,820,726 B2
(45) Date of Patent: Sep. 2, 2014

(54) ABUTMENT FIXING APPARATUS

(76) Inventor: Myong Hee Yeom, Daejeon (KR)

( * ) Notice: Subject to any disclaimer, the term of this patent is extended or adjusted under 35 U.S.C. 154(b) by 0 days.

(21) Appl. No.: 13/608,789

(22) Filed: Sep. 10, 2012

(65) Prior Publication Data
US 2013/0157222 A1  Jun. 20, 2013

(30) Foreign Application Priority Data

Dec. 16, 2011  (KR) .......................... 10-2011-0136303

(51) Int. Cl.
*A61C 13/225* (2006.01)
(52) U.S. Cl.
USPC ............................... 269/55; 269/249; 269/47
(58) Field of Classification Search
USPC .......... 269/143, 249, 37, 47, 53; 279/76, 91
See application file for complete search history.

(56) References Cited

U.S. PATENT DOCUMENTS

| 1,522,587 A * | 1/1925 | Hallstrom ...................... 407/101 |
| 1,596,708 A * | 8/1926 | Bellows ........................ 81/124.6 |
| 1,783,541 A * | 12/1930 | Hogg et al. ..................... 279/77 |
| 2,969,243 A * | 1/1961 | Drazick ........................... 279/76 |
| 3,091,474 A * | 5/1963 | Boutros et al. ................. 279/97 |
| 3,557,419 A * | 1/1971 | Flannery ......................... 407/36 |
| 3,663,028 A * | 5/1972 | King et al. ....................... 279/91 |
| 3,762,732 A * | 10/1973 | Speed ............................ 279/102 |
| 3,861,867 A * | 1/1975 | Ouhl ............................... 432/258 |
| 4,057,260 A * | 11/1977 | Sigott ............................. 279/77 |
| 4,133,545 A * | 1/1979 | Komori ............................ 279/83 |
| 4,140,305 A * | 2/1979 | Rabin .............................. 269/47 |
| 4,349,929 A * | 9/1982 | Dewey ............................... 7/158 |
| 4,402,519 A * | 9/1983 | Meaden et al. .................. 279/76 |
| 4,621,821 A * | 11/1986 | Schneider ....................... 279/83 |
| 5,096,212 A * | 3/1992 | Walsh ............................. 279/9.1 |
| 5,873,682 A * | 2/1999 | Tripsa ........................... 407/101 |
| 6,332,619 B1* | 12/2001 | DeRosa ........................... 279/76 |
| 6,394,465 B1* | 5/2002 | Guy .............................. 279/9.1 |
| 6,454,277 B1* | 9/2002 | Yu ................................... 279/49 |
| 6,543,318 B1* | 4/2003 | Erickson ........................ 82/1.11 |

(Continued)

FOREIGN PATENT DOCUMENTS

| EP | 1728485 A2 | 6/2006 |
| JP | 2007-229127 A | 9/2007 |

(Continued)

OTHER PUBLICATIONS

Search report issued in related application EP12168718, Feb. 21, 2013, 6 pages.

*Primary Examiner* — Lee D Wilson
*Assistant Examiner* — Tyrone V Hall, Jr.
(74) *Attorney, Agent, or Firm* — Drinker Biddle & Reath LLP

(57) ABSTRACT

An abutment fixing apparatus comprising a holder, a body connected to the body, and at least one installation recess into which at least one abutment is inserted. The abutment fixing apparatus further comprises at least one fixing unit connected to the body and fixing the abutment at a desire position of the at least one installation recess, and the at least one fixing unit moves the abutment in a direction equal to an insertion direction of the abutment into the at least one installation recess or applies a pressure to an entire external surface of a portion of the abutment, which is covered with the at least one fixing unit, to fix the abutment at the desired position of the at least one installation recess.

9 Claims, 6 Drawing Sheets

(56) References Cited

U.S. PATENT DOCUMENTS

| | | | |
|---|---|---|---|
| 7,007,574 B1 * | 3/2006 | Wu | 81/177.85 |
| 7,112,020 B2 * | 9/2006 | Sheffler et al. | 409/234 |
| 7,429,049 B2 * | 9/2008 | Kramer | 279/2.03 |
| 7,785,107 B2 | 8/2010 | Niznick | |
| 2006/0275729 A1 * | 12/2006 | Fornoff | 433/2 |
| 2007/0063456 A1 * | 3/2007 | Troxler | 279/156 |
| 2009/0275000 A1 * | 11/2009 | Jung et al. | 433/223 |
| 2011/0042880 A1 | 2/2011 | Konrad et al. | |

FOREIGN PATENT DOCUMENTS

| | | |
|---|---|---|
| JP | 2011-41809 A | 3/2011 |
| KR | 10-2010-0118544 A | 11/2010 |
| KR | 10-2011-0012568 A | 2/2011 |

* cited by examiner

ABUTMENT FIXING APPARATUS

CROSS-REFERENCE TO RELATED APPLICATIONS

This application claims priority to and the benefit of Korean Patent Application No. 10-2011-0136303 filed in the Korean Intellectual Property Office on Dec. 16, 2011, the entire content of which is incorporated herein by reference.

FIELD OF THE INVENTION

Embodiments relate to an abutment fixing apparatus.

BACKGROUND

An implant is an artificial tooth implanted into an alveolus when a tooth is lost or damaged. The implant has the following advantages: it allows only a lost or damaged tooth to be replaced without sacrificing adjacent teeth, it allows the artificial tooth to function like a natural tooth, it looks and feels like a natural tooth, it allows a patient to speak clearly after an operation, and it quickly improves a patient's oral health.

A general implant comprises a fixture embedded in the gum, an abutment fixed to the fixture by using a screw, and a crown fixed onto the abutment so as to give an external form of an artificial tooth. In this case, the abutment supports the crown.

According to Korean Patent No. 10-0981463, the abutment (hereinafter, referred to as a processing object) transfers a load from a crown to a fixture; that is, it functions to transfer a load to the jawbone. For this reason, the processing object should be manufactured considering not only a size, a shape, and a contour of an artificial tooth but also the occlusion with adjacent teeth and an opposing tooth (an upper tooth or lower tooth), and dental characteristics, conditions of the gum, and the gum line of an individual.

Accordingly, as for the processing object material of the implant, customized products manufactured so as to correspond to patient's teeth are preferred to handed-down products having fixed sizes.

SUMMARY

Accordingly, an embodiment of the invention provides an abutment fixing apparatus precisely clamping a processing abutment to be processed into a customized abutment in an artificial tooth processing device.

Another embodiment of the invention provides an abutment fixing apparatus easily being attached and detached, and having high precision, repeatability, and reproducibility.

In one aspect, there is an abutment fixing apparatus comprising a holder, a body connected to the body, at least one installation recess into which at least one abutment is inserted, and at least one fixing unit connected to the body and fixing the abutment at a desire position of the at least one installation recess, wherein the at least one fixing unit moves the abutment in a direction equal to an insertion direction of the abutment into the at least one installation recess or applies a pressure to an entire external surface of a portion of the abutment, which is covered with the at least one fixing unit, to fix the abutment at the desired position of the at least one installation recess.

The at least one fixing unit may comprise a fixing bolt connected to the abutment and a fixing recess functioning as a passage of the fixing bolt, and when the fixing bolt is operated, the abutment connected to the fixing bolt is moved into the installation in the direction equal to the insertion direction.

The abutment and the fixing bolt may be screw-connected to each other.

The at least one installation recess may be positioned and connected to the fixing recess, and a diameter of the at least one installation recess may be larger than a diameter of the fixing diameter.

The at least one fixing unit may comprise a tapered portion connected to the body and having plurality of recesses and a fixing nut connected to the tapered portion through a collet connection and having the installation recess, and the entire external surface of the portion of the abutment is covered with the tapered portion, and when the fixing nut is operated, widths of the recesses of the tapered portion decrease and the pressure is applied to the entire external surface of the portion of the abutment, which is covered or housed with the tapered portion.

The holder may comprise a combination recess positioned at the holder and a combination bolt inserted into the combination bolt, and wherein the abutment fixing apparatus further comprises a connection portion connected to the body and inserted into the combination recess, and the combination bolt clamps the connection portion inserted into the combination recess.

The connection portion may comprise a flat surface, and the flat surface is in contact with the combination bolt.

A diameter of the body may be larger than a diameter of the combination recess.

The body may comprise a plurality of installation recesses each into which the abutment is inserted, and the abutment fixing apparatus may comprise a plurality of fixing unit fixing the abutments inserted into the installation recesses at desire positions of the plurality of installation recesses, respectively.

The body may have a rectangular space at the body and the plurality of installation recesses may be positioned at a side adjacent to the rectangular space.

The body may have an L shape and the plurality of installation recesses may be positioned at different surfaces of the body.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Hereinafter, detailed embodiments of the invention will be described with reference to the accompanying drawings.

Figure 1:
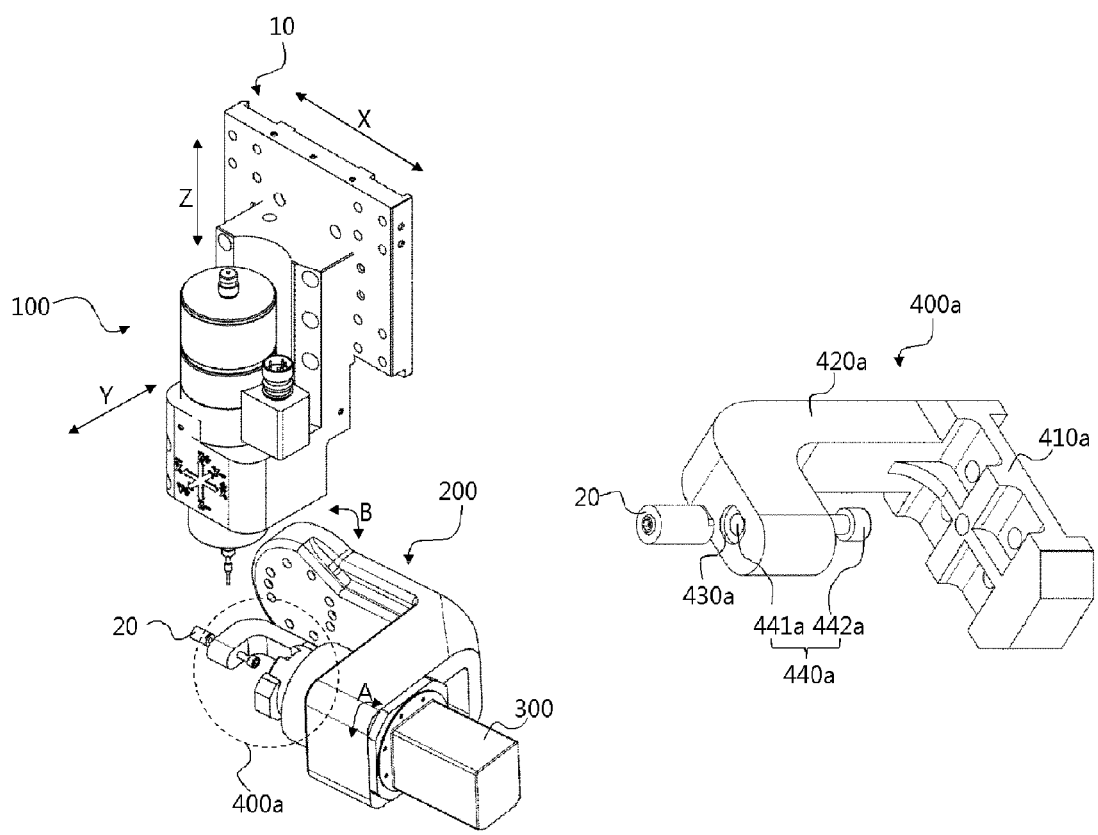
FIG. 1 is a diagram illustrating an artificial tooth processing apparatus equipped with an abutment fixing apparatus according to an exemplary embodiment of the invention.

FIG. 1 is a diagram illustrating an artificial tooth processing apparatus equipped with an abutment fixing apparatus according to an exemplary embodiment of the invention.

As shown in FIG. 1, an artificial tooth fixing apparatus comprises a spindle 100, a spindle arm 200 having a rotational shaft 300, and an abutment fixing apparatus 400a at which a processing object, hereinafter referred to as an abutment 20 is placed.

The spindle 100 comprises a processing space and elements placed at the processing space.

The spindle 100 may be moved in a direction of an X-axis (left and right), a direction of a Y-axis (back and forth), and a direction of a Z-axis (up and down) by a numerical control apparatus.

The spindle arm 200 includes the rotational shaft 300. The rotational shaft 300 performs a rotation (in FIG. 1, the rotation is shown as a 'B', and the rotation is called 'a B-axis rotation), that is, which rotates with respect to a central line which is in parallel with the Y-axis of the spindle 100 and a rotation (in FIG. 1, the rotation is shown as a 'A', and the rotation is called 'an A-axis rotation), that is, which rotates about a central line in parallel with the X-axis or Z-axis along with the B-axis rotation.

In this case, the abutment fixing apparatus 400a is combined with an upper portion of the rotational shaft 300 by using a holder.

The above-mentioned artificial tooth processing apparatus 10 is referred to as a five-axis processing apparatus because the processing directions are five including not only the X, Y and Z-axis of rotations, but also the A and B-axis of rotations. On the other hand, when one of the A-axis rotation and the B-axis rotation is excluded, the artificial tooth processing apparatus 10 is referred to as a four-axis processing apparatus.

As shown in FIG. 1, the abutment fixing apparatus 400a comprises a holder 410a to be combined with an upper portion of the rotational shaft 300 and an abutment installation unit 420a which has a '⌐' shape with the holder 410a and is formed at a portion (for example, an upper portion) of the abutment installation unit 420a.

The abutment installation unit 420a comprises a body of the '⌐' shape and an installation recess 430a formed at the body, and a fixing unit 440a positioned in the abutment installation unit 420a and connected to the installation recess 430a.

The body is connected to the holder 410.

The installation recess 430a is formed at a portion of the abutment installation unit 420a. The abutment 20 is inserted and received into the installation recess 430a. The portion at which the installation recess 430a is opposite to another surface combined with the holder 410a. Thus, the portion at which the installation recess 430a is formed is opposite to a portion of the abutment installation unit 420a connected to the holder 410a.

The fixing unit 440a clamps and installs the abutment 20 received into the installation recess 430a.

In this example, the fixing unit 440a comprises a fixing bolt 442a which clamps a lower portion (for example, a lower end portion) of the abutment 20 received into the installation recess 430a, and a fixing recess 441a positioned at a center portion of the installation recess 430a and serves as a passage of the fixing bolt 442a.

In this example, the installation recess 430a and the fixing recess 441a are connected to each other, and thereby, the installation recess 430a and the fixing recess 441a forms a hole penetrating the portion of the abutment installation unit 420a.

Since the abutment 20 is installed into the installation recess 430a, a diameter of the installation recess 430a is defined based on a diameter of the abutment 20, and since the fixing bolt 442a is inserted into the fixing recess 441a, a diameter of the fixing recess 441a is defined based on a diameter of the fixing bolt 442a.

For installing the abutment 20 into the installation recess 430a, the diameter of the installation recess 430a is larger than the diameter of the fixing recess 441a. Thereby, when the abutment 20 is positioned at a desired position into the installation recess 430a by an operation of the fixing bolt 442a of the fixing unit 440a, the abutment 20 is not moved into the fixing recess 441a because of a difference between the diameters of the installation recess 430a and the fixing recess 441a.

The lower portion of the abutment 20 may have a planar shape of any one of a letter 'D' shape, a polygonal shape, and a circular shape.

When the lower portion of the abutment 20 has the circular shape, the lower portion of the abutment 20 may have a fixing depression.

In this case, as described above, since the abutment 20 is inserted and received into the installation recess 430a, the installation recess 430a preferably has a planar shape of any one of a letter 'D' shape, a polygonal shape, and a circular shape, to correspond (that is, equal) to the planar shape of the lower portion of the abutment 20. Like the abutment 20, when the installation recess 430a has the planar shape of the circular shape, the installation recess 430a may have a fixing protrusion for combining with the fixing depression of the abutment 20. When the planar shape of the abutment 20 is the letter 'D' shape or the polygonal shape, the abutment 20 into the installation recess 430a of the letter 'D' shape or the polygonal shape is easily installed. However, when the abutment 20 is a circular planar shape, it is hard to find an exact installation position into the installation recess 430a. Thus, the abutment 20 is installed into the installation recess 430a by using the fixing depression of the abutment 20 and the fixing protrusion of the installation recess 430a.

Also, the holder 410a is coupled to the upper portion of the rotational shaft 300 by a bolt, etc.

An operation of the abutment fixing apparatus 400a is described in detail below.

The abutment 20 is inserted and received into the installation recess 430a and the fixing bolt 442a is inserted into the fixing recess 441a.

At this state, the fixing bolt 442a is operated (that is, rotated), and then, the abutment 20 is screw-connected to the fixing bolt 442a and the abutment 20 connected to the fixing bolt 442a is moved by the rotation of the fixing bolt 442a.

At this case, a position of the fixing bolt 442a may be changed or not changed according to the rotation operation of the fixing bolt 442a.

Thus, the abutment 20 is moved in a direction equal to an insertion direction of the abutment 20 into the installation recess 430a.

As described above, when the abutment 20 is moved to a desired position, the abutment 20 is not moved in spite of the operation of the fixing bolt 442a by the diameter difference between the installation recess 430a and the fixing recess 441a.

Thus, the abutment is safely installed into the installation recess 430a.

In this example, since the abutment 20 is moved along the insertion direction of the abutment 20, a position of the abutment into the installation recess 430a is also changed in the insertion direction and installed into the installation recess 430a. However, a central axis of the abutment 20 is not changed in spite of the movement of the abutment 20 by the fixing bolt 442a.

Accordingly, in the installation recess 430a, by the fixing bolt 442a of the fixing unit 440a, the abutment 20 is fixed and installed without the movement of the central axis of the abutment 20.

Next, referring to FIGS. 2 to 6, various examples of the abutment fixing apparatus of the artificial tooth processing apparatus according to an exemplary embodiment of the invention are described.

Figure 2:
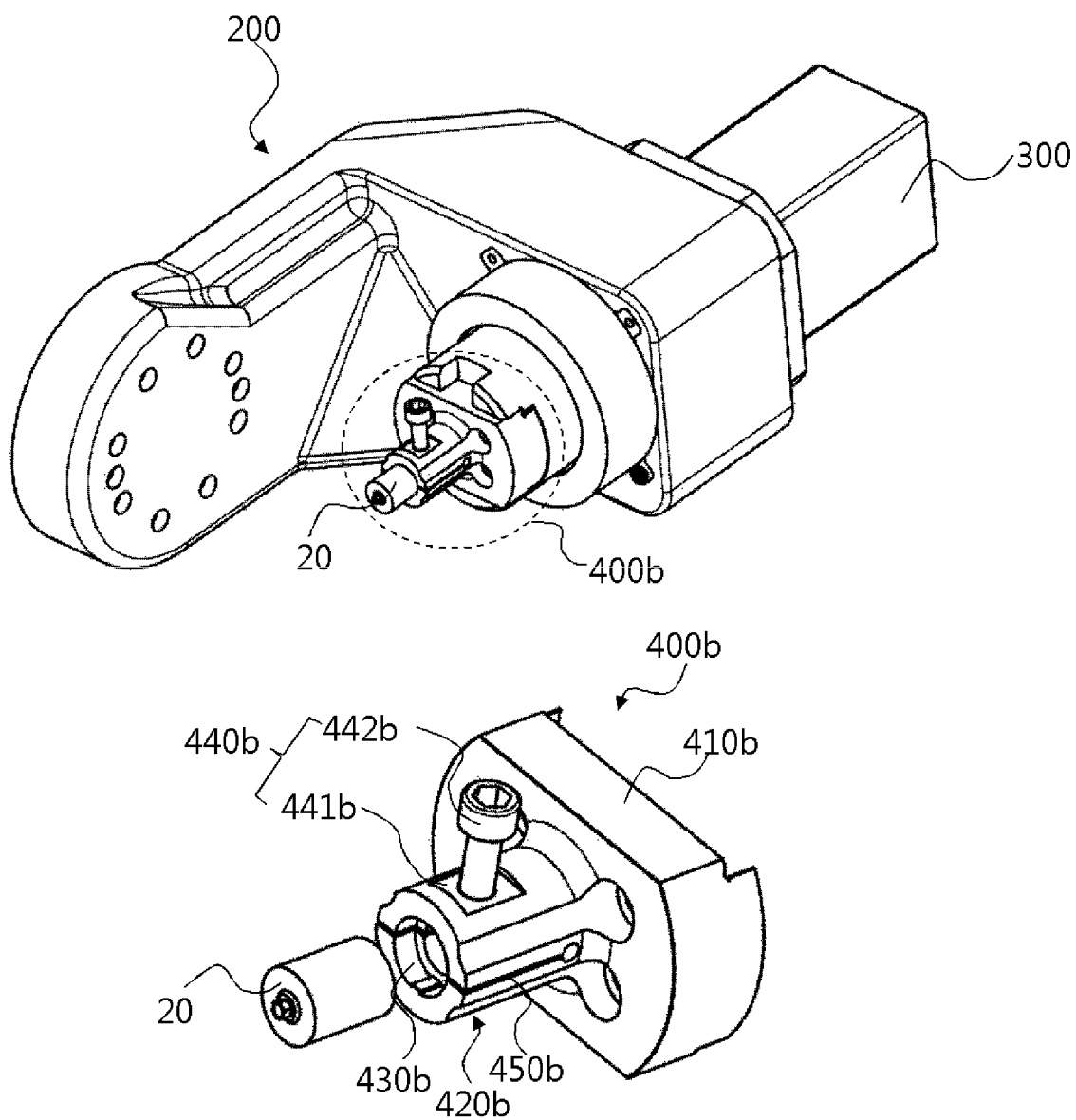
FIGS. 2 to 6 are diagrams illustrating various examples of an abutment fixing apparatus according to an exemplary embodiment of the invention, respectively.

First, as shown in FIG. 2, an abutment fixing apparatus 400b comprises a holder 410b to be combined with an upper portion of the rotational shaft 300 and an abutment installation unit 420b which has a round bracket shape (that is, a '( )' shape) and is perpendicularly coupled to a portion (for example, an upper portion) of the holder 410b.

Since the abutment installation unit 420b is formed as the round bracket shape, a space is formed in an internal portion of the abutment installation unit 420b, and the space is called an installation recess 430b in the example.

The installation recess 430b may have different diameter in accordance with a position of the installation recess 430b. Thus, as described above referring to FIG. 1, the abutment 20 may inserted only to a desired position by the diameter difference.

In FIG. 2, the installation recess 430b is positioned in an upper portion (or a left portion) of the abutment installation unit 420b, and the abutment 20 is inserted and received into the installation recess 430b.

The abutment installation unit 420b further comprises a body of the round bracket shape and a fixing unit 440b positioned in the body of the abutment installation unit 420b.

The body of the abutment installation unit 420b comprises at least one horizontal recess 450b which is positioned at least one portion of a side of the abutment installation unit 420b.

The body is connected to the holder 410b.

The fixing unit 440b clamps and fixes the abutment 20 received into the installation recess 430b at the desired position.

In this case, the fixing unit 440b comprises a fixing bolt 442b which clamps the abutment 20 by decreasing the width (or distance) of the horizontal recess 450b, and a fixing recess 441b which is a passage of the fixing bolt 442b.

The lower portion of the abutment 20 may have a planar shape of any one of a letter 'D' shape, a polygonal shape and a circular shape. When the lower portion of the abutment 20 has the circular shape, the lower portion of the abutment 20 may have a fixing depression.

In this case, as described above, since the abutment 20 is inserted and received into the installation recess 430b, the installation recess 430b has a planar shape of any one of a letter 'D' shape, a polygonal shape, and a circular shape, to correspond (that is, equal) to the planar shape of the lower portion of the abutment 20. Like the abutment 20, when the installation recess 430b has the planar shape of the circular shape, the installation recess 430b may have a fixing protrusion for combining with the fixing depression of the abutment 20.

When the planar shape of the abutment 20 is the letter 'D' shape or the polygonal shape, the abutment 20 into the installation recess 430b of the letter 'D' shape or the polygonal shape is easily installed. However, when the abutment 20 is a circular planar shape, it is hard to find an exact installation position into the installation recess 430b. Thus, the abutment 20 is installed into the installation recess 430b by using the fixing depression of the abutment 20 and the fixing protrusion of the installation recess 430b.

Also, the holder 410a is coupled to the upper portion of the rotational shaft 300 by using a bolt, etc.

An operation of the abutment fixing apparatus 400b is described in detail below.

The abutment 20 is inserted and received into the installation recess 430b and the fixing bolt 442a is inserted into the fixing recess 441a.

At this state, the fixing bolt 442a is operated (that is, rotated) and then, the width of the horizontal recess 450b decreases in proportion to a rotation amount of the fixing bolt 442a.

Thus, a diameter of the installation recess 430b is reduced by the rotation of the fixing bolt 442b and thereby, the abutment 20 inserted into the installation recess 430b is securely and safely fixed in the installation recess 430b without a position change of the abutment 20.

Accordingly, in the installation recess 430b, by the fixing bolt 442b of the fixing unit 440b, the abutment 20 is fixed without the movement of the central axis of the abutment 20. In this case, a position of the fixing bolt 442b may be changed or not changed according to the rotation operation of the fixing bolt 442b.

Figure 3:
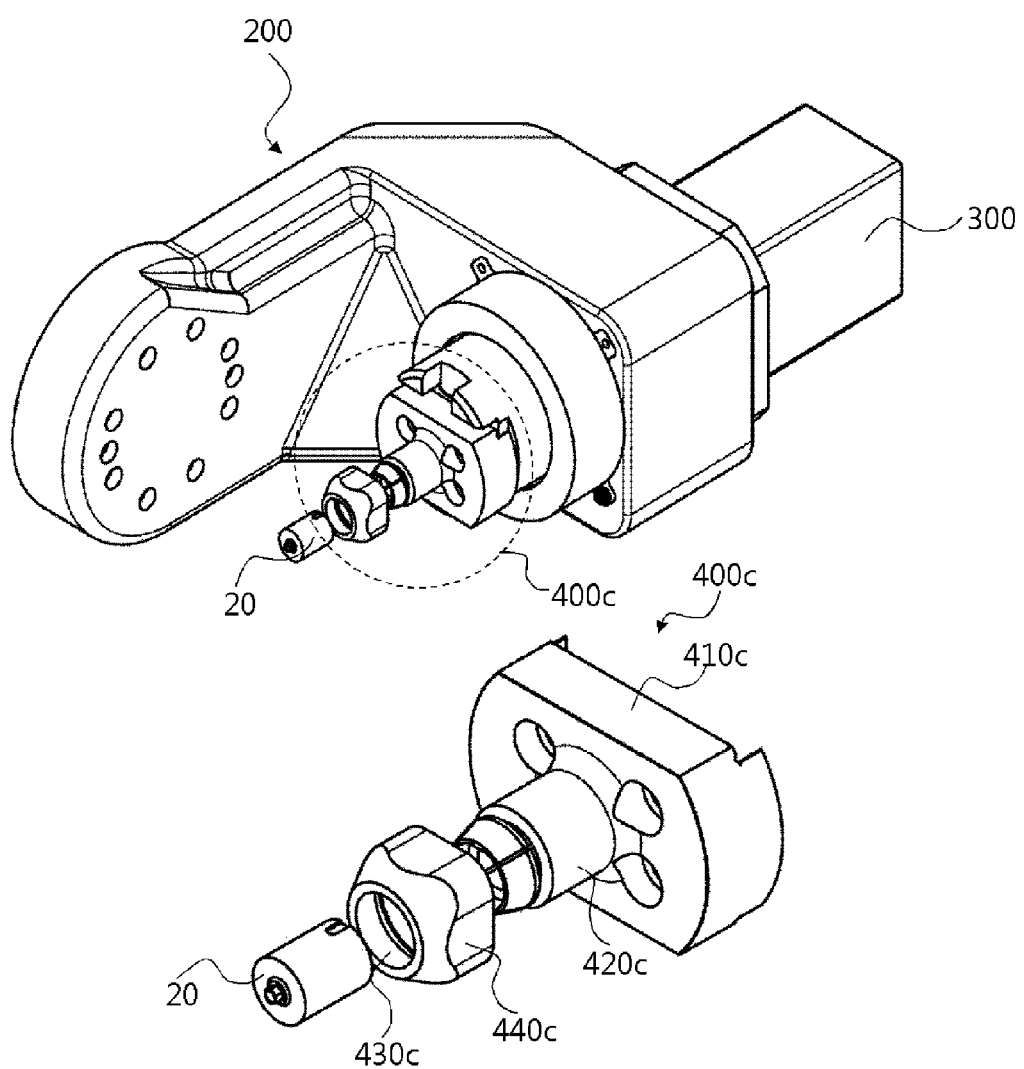

As illustrated in FIG. 3, an abutment fixing apparatus 400c according to another example comprises a holder 410c to be combined with an upper portion of the rotational shaft 300 and an abutment installation unit 420c which has a collet shape and is perpendicularly performed at a portion (for example, an upper portion) of the holder 410c.

The abutment installation unit 420c comprises a body connected to the portion of the holder 410c and a fixing unit.

The fixing unit comprises a tapered portion 423 connected to the body and a fixing nut 440c connected to the tapered portion.

The tapered portion 423 includes a plurality of recesses at the tapered portion 423, and thereby, a portion of the tapered portion 423 is divided into a plurality of parts from which is separated apart from by the recesses. In FIG. 3, the plurality of recesses are positioned in a horizontal direction, and thereby, the plurality of recesses are referred to as the plurality of horizontal recesses.

A diameter of the tapered portion 423 is changed in accordance with a position of the tapered portion 423. For example, in FIG. 3, the diameter of the tapered portion 423 increases from one portion (for example, an upper portion) adjacent to the fixing nut 440c to another portion (for example, a lower portion) facing the upper portion and connected to the body of the abutment installation unit 420c.

The fixing nut 440c includes an installation recess 430c in a center portion of the fixing nut 440c and clamps abutment 20 at an upper portion of the abutment installation unit 420c.

The installation recess 430c is formed in the upper portion of the abutment installation unit 420c and in the fixing nut 440c and the abutment 20 is received in the installation recess 430c.

The tapered portion 423 may form the collet shape of the abutment installation unit 420c, and the tapered portion 423 and the fixing nut 440c is connected by a collet connection.

The abutment 20 is inserted into the installation recess 430c and then inserted into a space in the tapered portion 423. The space is surrounded by the plurality of parts of the tapered portion 423 and formed.

The fixing nut 440c is inserted to the tapered portion 423 of through the installation recess 430c. The lower portion of the abutment 20 may have a planar shape of one of a letter 'D' shape, a polygonal shape, and a circular shape. When the lower portion of the abutment 20 has the circular shape, the lower portion of the abutment 20 may have a fixing depression.

In this case, as described above, since the abutment 20 is inserted and received into the installation recess 430c, the installation recess 430c has a planar shape of any one of a letter 'D' shape, a polygonal shape, and a circular shape, to correspond (that is, equal) to the planar shape of the lower portion of the abutment 20. Like the abutment 20, when the installation recess 430c has the planar shape of the circular shape, the installation recess 430c may have a fixing protrusion for combining with the fixing depression of the abutment 20.

When the planar shape of the abutment 20 is the letter 'D' shape or the polygonal shape, the abutment 20 into the installation recess 430c of the letter 'D' shape or the polygonal shape is easily installed. However, when the abutment 20 is a circular planar shape, it is hard to find an exact installation position into the installation recess 430c. Thus, the abutment 20 is installed into the installation recess 430c by using the fixing depression of the abutment 20 and the fixing protrusion of the installation recess 430c. Also, the holder 410a is coupled to the upper portion of the rotational shaft 300 by using a bolt, etc.

An operation of the abutment installation unit 420 is described below.

The abutment 20 is inserted and received into the installation recess 430b, and then, connected to the tapered portion 423 of the abutment installation unit 420c.

Next, the fixing nut 440c inserted to the tapered portion 423 through the installation recess 430c is operated, that is, rotated, and thereby, the widths of the plurality of horizontal recesses of the tapered portion 423 decrease in proportion to a rotation amount of the fixing nut 442c.

Thus, since a pressure occurred by the operation of the fixing nut 440c is applied to an entire external surface of the tapered portion 423, a diameter of the tapered portion 423 of the abutment installation unit 420c is reduced by the rotation of the fixing nut 442c. Thereby, the pressure is applied to an entire external surface of a portion of the abutment 20, which is covered or housed with the tapered portion 423 of the fixing unit, through the tapered portion 423 and the abutment 20 inserted into the installation recess 430c is stably and securely fixed and installed in the installation recess 430c without a position change of the abutment 20.

Accordingly, in the installation recess 430c, by the fixing nut 442c and the tapered portion 423, the abutment 20 is fixed without the movement of the central axis of the abutment 20.

Figure 4:
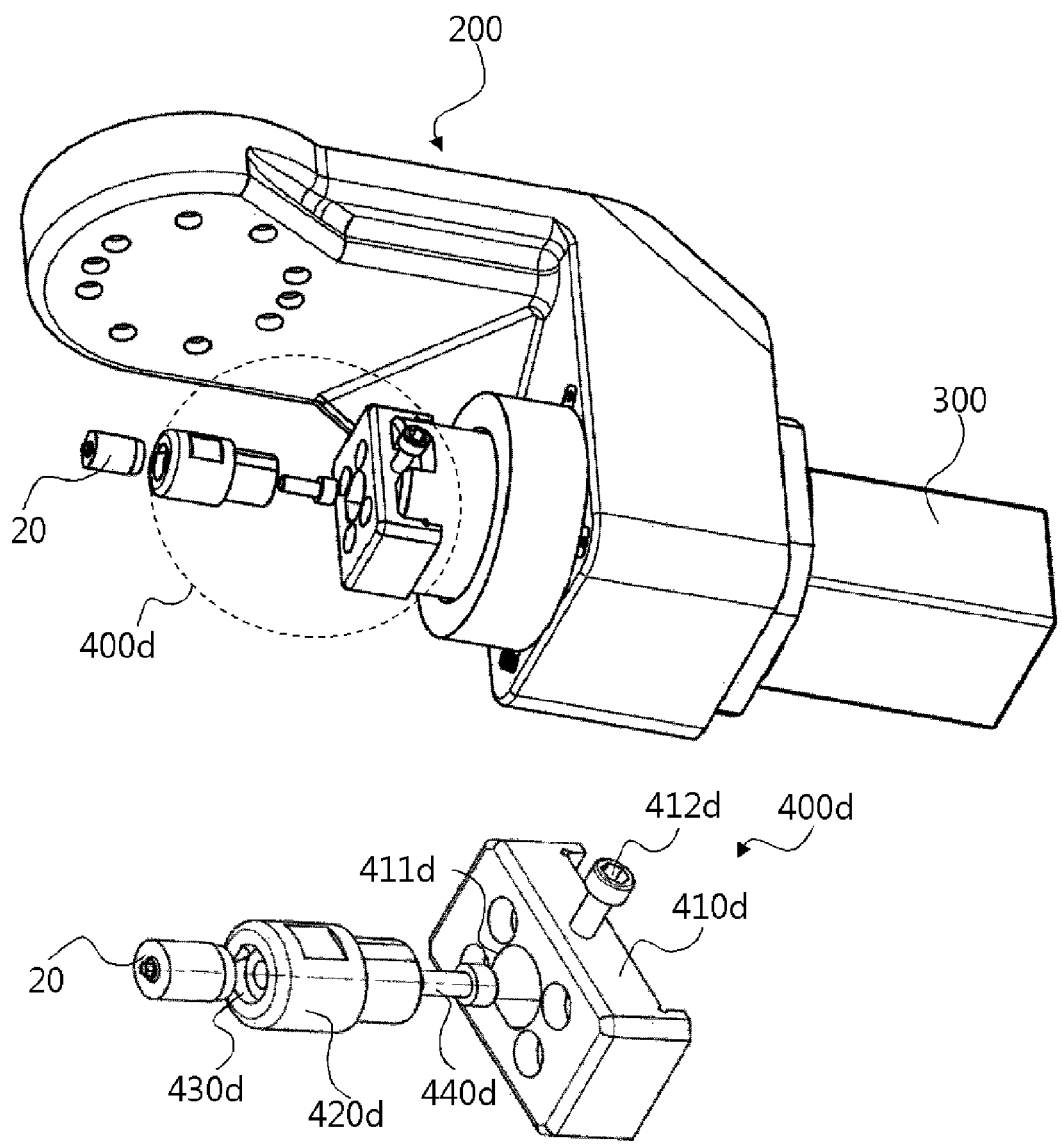

In FIG. 4, the abutment fixing apparatus 400d according to the example comprises a holder 410d to be combined with an upper portion of the rotational shaft 300, and an abutment installation unit 420d which is perpendicularly coupled to a portion (for example, an upper portion) of the holder 410d.

The holder 410d comprises a combination recess 411d formed at a central portion of the holder 410d and a combination bolt 412d which is positioned at a side surface of the holder 410d.

At this case, a surface at which the combination recess 411d forms substantially 90 degrees with the surface at which the combination bolt 412d is positioned.

The abutment installation unit 420d comprises a body having an installation recess 430d at a central portion of the body and fixing bolt 440d inserted into the installation recess 430d. The body is connected to the holder 410d.

The abutment installation unit 420d further comprises a connection portion 450 connected to the body of the abutment installation unit 420d and inserted into the combination recess 411d.

The fixing bolt 440d is positioned toward the connection portion 450 and clamps the abutment 20 inserted into the installation recess 430d.

A function of the fixing bolt 440d is equal to that of the fixing bolt 442a of FIG. 1, and thereby, the detailed description of the fixing bolt 440d is omitted.

In FIG. 4, the body of the abutment installation unit 420d has a cylinder shape, but an alternative example, the body may have a polyprism shape.

The connection portion 450 includes a flat portion 451 positioned at a portion of an external surface of the connection portion 450.

The connection portion 450 is inserted into the combination recess 411d of the holder 410d, and thereby, the abutment installation unit 420d is connected to the holder 410d by using the combination recess 411d and fixed into the combination recess 411d contacting with the flat surface of the connection portion 450 by using the combination bolt 412d.

That is, the combination bolt 421d clamps the flat surface 451 of the connection portion 450 inserted into the combination recess 411d and fixes the abutment installation unit 420d.

Thus, since the combination bolt 421d is in contact with the flat surface 451, instead of a rounded surface of the connection portion and performs the clamping operation, the clamping operation of the combination bolt 421d is stably, easily and accurately performed.

In this example, since the connection portion 450 is inserted into the combination recess 411d, a diameter of the connection portion 450 is smaller than a diameter of the combination recess 411d. At this case, a shape of the connection portion 450 may be equal to a shape of the combination recess 411d.

Further, a diameter of the body of the abutment installation unit 420d is larger than a diameter of the combination recess 411d. Thus, it is prevented that a undesired portion, that is, the body of the abutment installation unit 420d is inserted into the combination recess 411d. Thereby, by a diameter difference between the abutment installation unit 420d and the combination recess 411d, the abutment installation unit 420d is easily and exactly connected to the holder 410d at a desired position.

Except the connection portion 450, the abutment installation unit 420d, a function of the abutment installation unit 420d is equal to functions of the abutment installation unit 420 and 420a-420c. Thus, a structure of the abutment installation unit 420d for fixing the abutment 20 to the abutment installation unit 420d by using the fixing bolt 440d may be one of FIGS. 1 to 3. And, the lower portions of the abutment 20 and the abutment installation recess 420d may have a planar shape of any one of a letter 'D' shape, a polygonal shape, and a circular shape. When the lower portion of the abutment 20 and the abutment installation unit 420d has the circular shape, the lower portion of the abutment 20 and abutment installation unit 420d may have a fixing depression. In this case, the combination recess 411d and the installation recess 430d have a planar shape of any one of a letter 'D' shape, a polygonal shape, and a circular shape with a fixing protrusion for combining with the fixing depression of the abutment 20 therein. That is, the planar shape of the combination recess 411d and the installation recess 430d corresponds to the planar shape of the lower end portions of the abutment 20 and the abutment installation unit 420d.

When the planar shape of the abutment 20 is the letter 'D' shape or the polygonal shape, the abutment 20 into the installation recess 430d of the letter 'D' shape or the polygonal shape is easily installed. However, when the abutment 20 is a circular planar shape, it is hard to find an exact installation position into the installation recess 430d. Thus, the abutment 20 is installed into the installation recess 430d by using the fixing depression of the abutment 20 and the fixing protrusion of the installation recess 430d.

Also, the holder 410d is coupled to the upper portion of the rotational shaft 300 by using a bolt, etc.

An operation of the abutment installation unit 420d except the connection portion 450 is equal to that of the operation of the abutment installation unit 420 or 420a-420c, and thereby, the operation of the abutment installation unit 420d.

The connection portion 450 is inserted into the combination recess 411d of the holder 410.

Then, the combination bolt 412d is operated or rotated, and then the combination bolt 412d is downwardly moved and clamps the flat surface 451 of the connection portion 450.

Thereby, the abutment installation unit 420d is easily attached to the holder 410d.

For detaching the abutment installation unit 420d from the holder 410d, the combination bolt 412d is operated or rotated in the opposite direction to a direction for attaching the abutment installation unit 420d to the holder 410d. Then, the combination bolt 412d is upwardly moved.

Thereby, a clamping state by using the combination bolt 412d is released and thereby, the abutment installation unit 420d inserted into the combination recess 411d is easily detached from the holder 410d.

Figure 5:
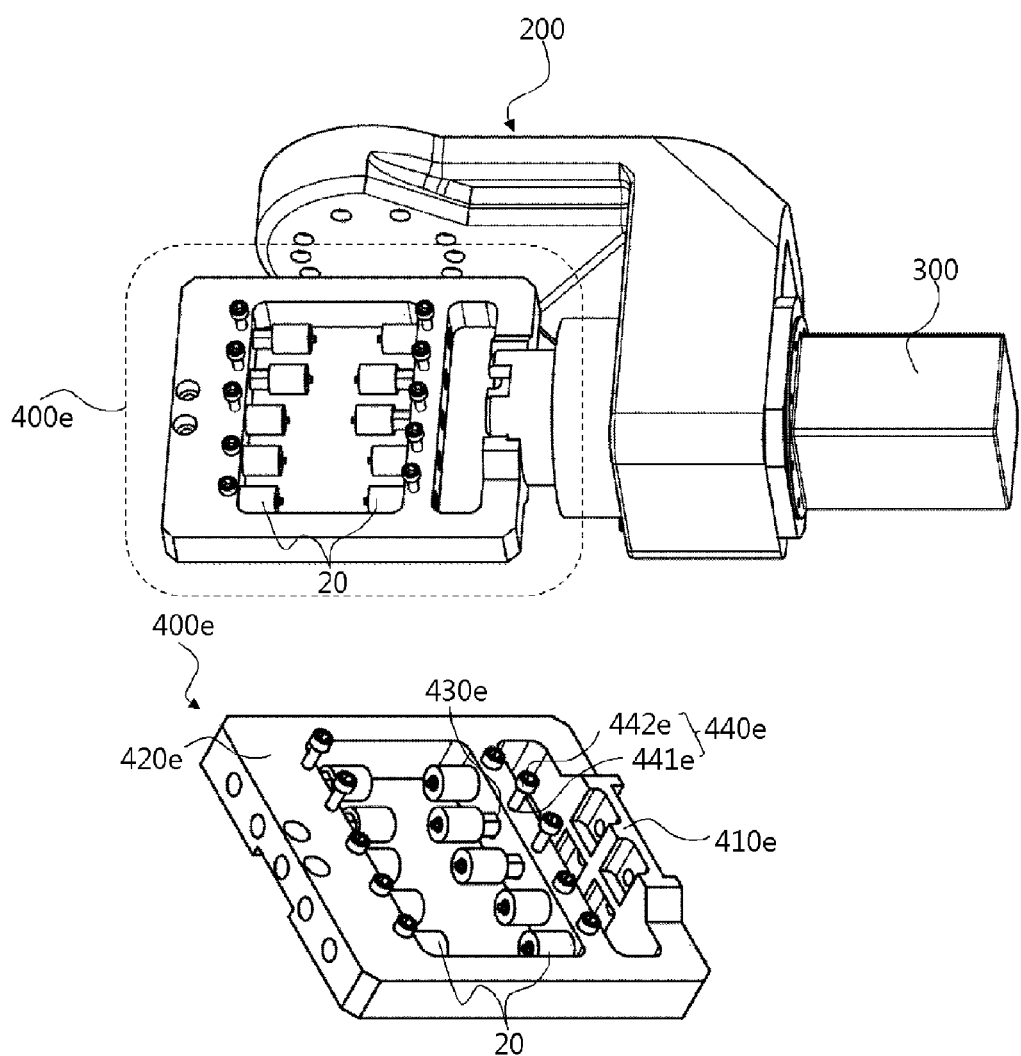

As shown in FIG. 5, a abutment fixing apparatus 400e according to this example comprises a holder 410e to be combined with an upper portion (or an end portion) of the rotational shaft 300 and an abutment installation unit 420e which is connected to the holder 410e and has a plate shape with an open rectangular space (with short sides and long sides).

The abutment installation unit 420e comprises a body having a plurality of installation recesses 430e and a plurality of fixing unit 440e.

The plurality of installation recesses 430e are positioned at a side adjacent to the rectangular space.

The body is connected to the holder 410e.

In FIG. 5, the plurality of installation recesses 430e are arranged along the long side of the space of the abutment installation unit 420e.

An abutment 20 is inserted and installed into each installation recess 430a.

Each of the fixing units 440e comprises a fixing recess 410e formed at the abutment installation unit 420e and a fixing bolt 442e inserted into the fixing recess 441e.

The fixing bolt 442e clamps the abutment 20 and the fixing recess 441e functions as a passage of the fixing bolt 442e.

Similar to the fixing unit 440b of FIG. 2, the fixing unit 440e of the example also claims the abutment 20 using the fixing bolt 442e.

Thus, the fixing bolt 442e is operated (that is, rotated) inserted into the fixing recess 441e, and then the fixing bolt 442e is downwardly or upwardly into the fixing recess 441e in accordance with a rotation direction of the fixing bolt 442e. Thereby, the fixing bolt 442e clamps the abutment 20 or releases a clamping state. Accordingly, the abutment 20 is easily and securely installed into the installation recess 430e.

However, unlike the examples shown in FIGS. 1 to 4, the abutment installation unit 420a includes the plurality of installation recesses 430e and the plurality of fixing unit 440e, and thereby, the plurality of abutments 20 are installed at the abutment installation unit 420e. Thus, since the plurality of abutments 20 are processed at the same time, efficiency and productivity are improved.

The lower portion of the abutment 20 may have a planer shape of any one of a letter 'D' shape, a polygonal shape, and a circular shape. When the lower portion of the abutment 20 has the circular shape, the lower portion of the abutment 20 may have a fixing depression.

In this case, the installation recess 430e may have a planar shape of any one of a letter 'D' shape, a polygonal shape, and a circular shape with a fixing protrusion for combining with the fixing depression of the abutment 20 therein, and its planar shape preferably corresponds to the planar shape of the lower portion of the abutment 20.

When the planar shape of the abutment 20 is the letter 'D' shape or the polygonal shape, the abutment 20 into the installation recess 430e of the letter 'D' shape or the polygonal shape is easily installed. However, when the abutment 20 is a circular planar shape, it is hard to find an exact installation position into the installation recess 430e. Thus, the abutment 20 is installed into the installation recess 430e by using the fixing depression of the abutment 20 and the fixing protrusion of the installation recess 430e.

Also, the holder 410e is coupled to the upper portion of the rotational shaft 300 by using a bolt, etc.

Figure 6:
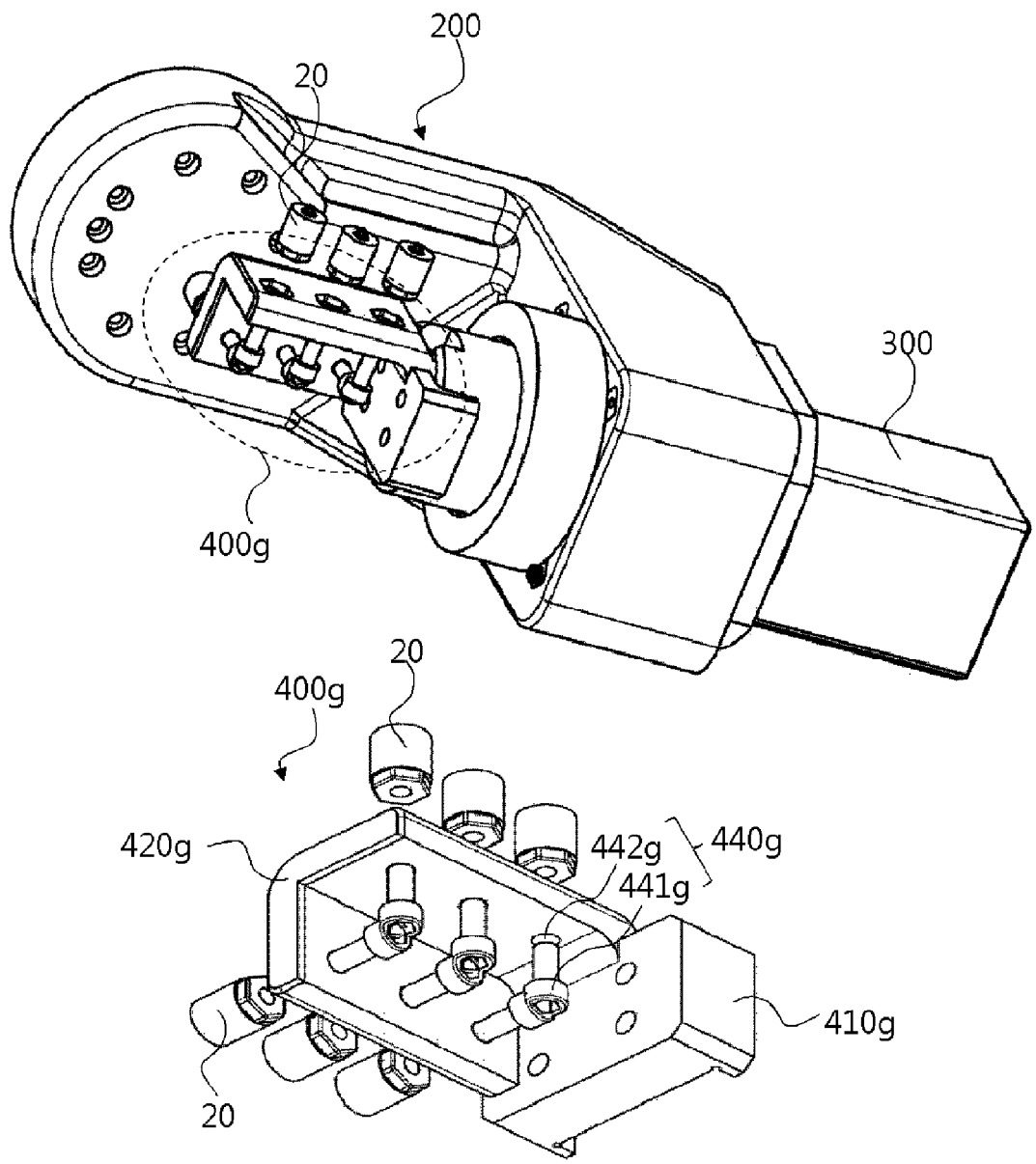

FIG. 6 shows another example of an abutment installation unit 420g for installing a plurality of abutments 20.

Thereby, as illustrated in FIG. 6, the abutment fixing apparatus 400g according to this example comprises a holder 410g to be combined with an upper portion (or an end portion) of the rotational shaft 300 and an abutment installation unit 420g which has a letter 'L' shape and is perpendicularly coupled to a portion (for example, an upper portion) of the holder 410g.

The abutment installation unit 420g comprises a body of the 'L' shape and having one or more installation recesses (not illustrated) which are formed in an outside surface (an external surface) of the abutment installation unit 420g and which receive the abutment 20 therein, and a fixing unit 440g which clamps the abutment 20 inserted into the installation recesses and is located under the abutment installation unit 420g. The body is connected to the holder 410g.

As shown in FIG. 6, the number of the fixing unit 440g and the installation recesses are plural, respectively.

The plurality of fixing units 440g and the plurality of installation recesses are positioned at different surfaces, for example, at an upper surface and a side surface of the abutment installation unit 420g in FIG. 6.

Each fixing unit 440g comprises a fixing bolt 441g which clamps the lower portion of the abutment 20 and a fixing recess 442g which is formed at a center portion of the installation recess and serves as a passage of the fixing bolt 441g.

In this example, the installation recess and the fixing recess 442g are connected to each other, and thereby, the installation recess and the fixing recess 442g forms a hole penetrating the portion of the abutment installation unit 420g.

Since the abutment 20 is installed into the installation recess, a diameter of the installation recess is defined based on a diameter of the abutment 20, and since the fixing bolt 441g is inserted into the fixing recess 442g, a diameter of the fixing recess 442g is defined based on a diameter of the fixing recess 442g.

Thereby, as already described referring to FIG. 1, the abutment 20 is stably installed at a desired position of the fixing recess 442g because of a difference between the diameters of the installation recess and the fixing recess 442g.

Structures and operations of the installation recess and the fixing unit 440g may be the same as those of the FIG. 1.

Thus, the abutment 20 is inserted and installed into the each installation recesses and each fixing unit 440g clamps each abutment 20 inserted into each installation recess by using the fixing bolt 441g connected to the abutment 20 by a screw connection, etc.

That is, each fixing bolt 441g is operated (that is, rotated), and then, each abutment 20 is moved upward or downward, or frontward or backward.

Thus, since the abutment 20 is moved along the insertion direction of the abutment 20, a position of the abutment into the installation recess is also changed in the insertion direction and securely and stably installed into the installation recess. However, a central axis of the abutment 20 is not changed in spite of the movement of the abutment 20 by the fixing bolt 441g.

Accordingly, by the fixing bolt 441g of the fixing unit 440g, the abutment 20 is fixed and installed without the movement of the central axis of the abutment 20.

In this case, a position of the fixing bolt 441g may be changed or not changed according to the rotation operation of the fixing bolt 441g.

Like the example shown in FIG. 5, the abutment installation unit 420g comprises the plurality of installation recesses and the plurality of fixing units 440g, and thereby, the plurality of abutments 20 are installed at the abutment installation unit 420g. Thus, since the plurality of abutments 20 are processed at the same time, when an efficiency and productivity increase.

And, the lower portion of the abutment 20 may have a planar shape of any one of a letter 'D' shape, a polygonal shape, and a circular shape. When the lower portion of the abutment 20 has the circular shape, the lower portion of the abutment 20 may have a fixing depression. In this case, the installation recess may have a planar shape of any one of a letter 'D' shape, a polygonal shape, and a circular shape with a fixing protrusion for combining with the fixing depression of the abutment 20 therein, and its planar shape preferably corresponds to the planar shape of the lower end portion of the abutment 20.

When the planar shape of the abutment 20 is the letter 'D' shape or the polygonal shape, the abutment 20 into the installation recess of the letter 'D' shape or the polygonal shape is easily installed. However, when the abutment 20 is a circular planar shape, it is hard to find an exact installation position into the installation recess. Thus, the abutment 20 is installed into the installation recess by using the fixing depression of the abutment 20 and the fixing protrusion of the installation recess.

Also, the holder 410g is coupled to the upper portion of the rotational shaft 300 by using a bolt, etc.

Although embodiments have been described with reference to a number of illustrative embodiments thereof, it should be understood that numerous other modifications and embodiments can be devised by those skilled in the art that will fall within the scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An abutment fixing apparatus comprising:
a holder;
a body connected to the holder;
at least one installation recess into which at least one abutment is inserted; and
at least one fixing unit connected to the body, removably attachable to the abutment, and fixing the abutment at a desired position of the at least one installation recess,
wherein upon attachment to the abutment, the at least one fixing unit moves the abutment in a direction equal to an insertion direction of the abutment into the at least one installation recess to fix the abutment at the desired position of the at least one installation recess.

2. The abutment fixing apparatus of claim 1, wherein the at least one fixing unit comprises a fixing recess formed in an equal direction to a formed direction of the at least one installation recess and connected to the at least one installation recess, and a fixing bolt inserted into the fixing recess,
wherein when the abutment is inserted into the at least one installation recess, the fixing bolt is screw-connected to the abutment to attach the abutment to the fixing bolt, and by an operation of the fixing bolt, the abutment screw-connected to the fixing bolt is moved into the installation recess in the direction equal to the insertion direction of the abutment.

3. The abutment fixing apparatus of claim 2, wherein a diameter of the at least one installation recess is larger than a diameter of the fixing recess.

4. The abutment fixing apparatus of claim 2, wherein the abutment is moved into the installation recess without a movement of a central axis of the abutment.

5. The abutment fixing apparatus of claim 1, further comprising:
a combination recess positioned at a first surface of the holder;
a connection portion connected to the body and inserted into the combination recess; and
a combination bolt inserted into a second surface of the holder which is intersected with the first surface and clamping or detaching the connection portion inserted into the combination recess by downwardly or upwardly movement according to a rotation operation.

6. The abutment fixing apparatus of claim 5, wherein the connection portion comprises a flat surface in contact with the combination bolt.

7. The abutment fixing apparatus of claim 1, wherein the abutment is moved into the installation recess without a movement of a central axis of the abutment.

8. An abutment fixing apparatus comprising:
a holder;
a body connected to the holder;
at least one installation recess into which at least one abutment is inserted; and
at least one fixing unit connected to the body and fixing the abutment at a desired position of the at least one installation recess,
wherein the at least one fixing unit moves the abutment in a direction equal to an insertion direction of the abutment into the at least one installation recess to fix the abutment at the desired position of the at least one installation recess;
wherein the at least one fixing unit comprises a tapered portion connected to the body and having a plurality of recesses and a fixing nut connected to the tapered portion through a collet connection and having the installation recess, and the external surface of the portion of the abutment is covered with the tapered portion, and
when the fixing nut is operated, widths of the recesses of the tapered portion decrease and the pressure is applied to the external surface of the portion of the abutment, which is covered or housed with the tapered portion.

9. An abutment fixing apparatus comprising:
a holder;
a body connected to the holder;
at least one installation recess into which at least one abutment is inserted; and
at least one fixing unit connected to the body and fixing the abutment at a desired position of the at least one installation recess,
wherein the at least one fixing unit moves the abutment in a direction equal to an insertion direction of the abutment into the at least one installation recess to fix the abutment at the desired position of the at least one installation recess;
wherein the body has an L shape and a plurality of installation recesses are positioned at different surfaces of the body.

* * * * *